United States Patent [19]

Tsai et al.

[11] Patent Number: 6,015,704
[45] Date of Patent: Jan. 18, 2000

[54] MUTANT ASPARTASE AND THE PREPARATION THEREOF

[75] Inventors: Hsin Tsai; Jin-Tann Chen; Hsiu-Hui Chen, all of Taipei, Taiwan

[73] Assignee: Development Center for BioTechnology, Taipei, Taiwan

[21] Appl. No.: 08/843,982

[22] Filed: Apr. 18, 1997

[30] Foreign Application Priority Data

Jan. 31, 1997 [CN] China .................................. 86101167

[51] Int. Cl.⁷ ..................................... C12N 9/88
[52] U.S. Cl. .......................... 435/232; 435/106; 435/109; 435/252.33; 536/23.2
[58] Field of Search ................................. 435/232, 252.3, 435/252.33, 320.1, 106, 109; 536/23.2, 23.7

[56] References Cited

PUBLICATIONS

Zhang et al. "Enzymatic genration of mutant libraries in vivo for random mutagensis of aspartase gene" Chines Science Bulletin 37 (7), 598–601; Apr. 1992.

Yumoto, et al *Physiol. Chem. Phys.* 14 391–397 (1982) Studies on Aspartase VIII. Protease–Mediated Activation: Comparative Survey of Protease Specificity for Activation and Peptide Cleavage.

Murase, et al *Biochem. Biophys. Res. Commun.* 177 No. 1 414–419 (1991) Activation of Aspartase By Site–Directed Mutagenesis.

Zhang, et al *Biochem. Biophys. Res. Commun.* 192 No. 1 15–21 (1993) Z Enhancement of the Stability and Activity of Aspartase By Random and Site–Directed Mutagenesis.

*Primary Examiner*—Ponnathapura Achutamurthy
*Assistant Examiner*—Nashaat T. Nashed
*Attorney, Agent, or Firm*—Ladas & Parry

[57] ABSTRACT

Disclosed is a mutant aspartase comprising the amino acid sequence of a wild-type *E. coli* aspartase wherein the amino acid residue at one of positions 25, 123, 421 and 463 is substituted. Also disclosed is a process for preparing the above mutant aspartase.

7 Claims, 9 Drawing Sheets

```
Ser Asn Asn Ile Arg Ile Glu Glu Asp Leu
1               5                   10

Leu Gly Thr Arg Glu Val Pro Ala Asp Ala
                15                  20

Tyr Tyr Gly Val His Thr Leu Arg Ala Ile
                25                  30

Glu Asn Phe Tyr Ile Ser Asn Asn Lys Ile
                35                  40

Ser Asp Ile Pro Glu Phe Val Arg Gly Met
                45                  50

Val Met Val Lys Lys Ala Ala Ala Met Ala
                55                  60

Asn Lys Glu Leu Gln Thr Ile Pro Lys Ser
                65                  70

Val Ala Asn Ala Ile Ile Ala Ala Cys Asp
                75                  80

Glu Val Leu Asn Asn Gly Lys Cys Met Asp
                85                  90

Gln Phe Pro Val Asp Val Tyr Gln Gly Gly
                95                  100
```

FIG. 1A

```
Ala Gly Thr Ser Val Asn Met Asn Thr Asn
                105                 110

Glu Val Leu Ala Asn Ile Gly Leu Glu Leu
                115                 120

Met Gly His Gln Lys Gly Glu Tyr Gln Tyr
                125                 130

Leu Asn Pro Asn Asp His Val Asn Lys Cys
                135                 140

Gln Ser Thr Asn Asp Ala Tyr Pro Thr Gly
                145                 150

Phe Arg Ile Ala Val Tyr Ser Ser Leu Ile
                155                 160

Lys Leu Val Asp Ala Ile Asn Gln Leu Arg
                165                 170

Glu Gly Phe Glu Arg Lys Ala Val Glu Phe
                175                 180

Gln Asp Ile Leu Lys Met Gly Arg Thr Gln
                185                 190

Leu Gln Asp Ala Val Pro Met Thr Leu Gly
                195                 200
```

FIG. 1B

```
Gln Glu Phe Arg Ala Phe Ser Ile Leu Leu
                205                 210

Lys Glu Glu Val Lys Asn Ile Gln Arg Thr
                215                 220

Ala Glu Leu Leu Leu Glu Val Asn Leu Gly
                225                 230

Ala Thr Ala Ile Gly Thr Gly Leu Asn Thr
                235                 240

Pro Lys Glu Tyr Ser Pro Leu Ala Val Lys
                245                 250

Lys Leu Ala Glu Val Thr Gly Phe Pro Cys
                255                 260

Val Pro Ala Glu Asp Leu Ile Glu Ala Thr
                265                 270

Ser Asp Cys Gly Ala Tyr Val Met Val His
                275                 280

Gly Ala Leu Lys Arg Leu Ala Val Lys Met
                285                 290

Ser Lys Ile Cys Asn Asp Leu Arg Leu Leu
                295                 300
```

FIG. 1C

Ser Ser Gly Pro Arg Ala Gly Leu Asn Glu
            305                 310

Ile Asn Leu Pro Glu Leu Gln Ala Gly Ser
            315                 320

Ser Ile Met Pro Ala Lys Val Asn Pro Val
            325                 330

Val Pro Glu Val Val Asn Gln Val Cys Phe
            335                 340

Lys Val Ile Gly Asn Asp Thr Thr Val Thr
            345                 350

Met Ala Ala Glu Ala Gly Gln Leu Gln Leu
            355                 360

Asn Val Met Glu Pro Val Ile Gly Gln Ala
            365                 370

Met Phe Glu Ser Val His Ile Leu Thr Asn
            375                 380

Ala Cys Tyr Asn Leu Leu Glu Lys Cys Ile
            385                 390

Asn Gly Ile Thr Ala Asn Lys Glu Val Cys
            395                 400

FIG. 1D

```
Glu Gly Tyr Val Tyr Asn Ser Ile Gly Ile
                405                 410

Val Thr Tyr Leu Asn Pro Phe Ile Gly His
                415                 420

His Asn Gly Asp Ile Val Gly Lys Ile Cys
                425                 430

Ala Glu Thr Gly Lys Ser Val Arg Glu Val
                435                 440

Val Leu Glu Arg Gly Leu Leu Thr Glu Ala
                445                 450

Glu Leu Asp Asp Ile Phe Ser Val Gln Asn
                455                 460

Leu Met His Pro Ala Tyr Lys Ala Lys Arg
                465                 470

Tyr Thr Asp Glu Ser Glu Gln
                475
```

FIG. 1E

| | | | |
|---|---|---|---|
| CTCGGGTATT | CGGTCGATGC | AGGGGATAAT | 30 |
| CGTCGGTCGA | AAAACATTCG | AAACCACATA | 60 |
| TATTCTGTGT | GTTTAAAGCA | AATCATTGGC | 90 |
| AGCTTGAAAA | AGAAGGTTCA | CATGTCAAAC | 120 |
| AACATTCGTA | TCGAAGAAGA | TCTGTTGGGT | 150 |
| ACCAGGGAAG | TTCCAGCTGA | TGCCTACTAT | 180 |
| GGTGTTCACA | CTCTGAGAGC | GATTGAAAAC | 210 |
| TTCTATATCA | GCAACAACAA | AATCAGTGAT | 240 |
| ATTCCTGAAT | TTGTTCGCGG | TATGGTAATG | 270 |
| GTTAAAAAAG | CCGCAGCTAT | GGCAAACAAA | 300 |
| GAGCTGCAAA | CCATTCCTAA | AAGTGTAGCG | 330 |
| AATGCCATCA | TTGCCGCATG | TGATGAAGTC | 360 |
| CTGAACAACG | GAAAATGCAT | GGATCAGTTC | 390 |
| CCGGTAGACG | TCTACCAGGG | CGGCGCAGGT | 420 |
| ACTTCCGTAA | ACATGAACAC | CAACGAAGTG | 450 |

FIG. 2A

| | | | |
|---|---|---|---|
| CTGGCCAATA | TCGGTCTGGA | ACTGATGGGT | 480 |
| CACCAGAAAG | GTGAATATCA | GTACCTGAAC | 510 |
| CCGAACGACC | ATGTTAACAA | ATGTCAGTCC | 540 |
| ACTAACGACG | CCTACCCGAC | CGGTTTCCGT | 570 |
| ATCGCAGTTT | ACTCTTCTCT | GATTAAGCTG | 600 |
| GTAGATGCGA | TTAACCAACT | GCGTGAAGGC | 630 |
| TTTGAACGTA | AAGCTGTCGA | ATTCCAGGAC | 660 |
| ATCCTGAAAA | TGGGTCGTAC | CCAGCTGCAG | 690 |
| GACGCAGTAC | CGATGACCCT | CGGTCAGGAA | 720 |
| TTCCGCGCTT | TCAGCATCCT | GCTGAAAGAA | 750 |
| GAAGTGAAAA | ACATCCAACG | TACCGCTGAA | 780 |
| CTGCTGCTGG | AAGTTAACCT | TGGCGCAACA | 810 |
| GCAATCGGTA | CTGGTCTGAA | CACGCCGAAA | 840 |
| GAGTACTCTC | CGCTGGCAGT | GAAAAAACTG | 870 |
| GCTGAAGTCA | CTGGCTTCCC | ATGCGTACCG | 900 |

FIG. 2B

| | | | |
|---|---|---|---|
| GCTGAAGACC | TGATCGAAGC | GACCTCTGAC | 930 |
| TGCGGCGCTT | ATGTTATGGT | TCACGGCGCG | 960 |
| CTGAAACGCC | TGGCTGTGAA | GATGTCCAAA | 990 |
| ATCTGTAACG | ACCTGCGCTT | GCTCTCTTCT | 1020 |
| GGCCCACGTG | CCGGCCTGAA | CGAGATCAAC | 1050 |
| CTGCCGGAAC | TGCAGGCGGG | CTCTTCCATC | 1080 |
| ATGCCAGCTA | AAGTAAACCC | GGTTGTTCCG | 1110 |
| GAAGTGGTTA | ACCAGGTATG | CTTCAAAGTC | 1140 |
| ATCGGTAACG | ACACCACTGT | TACCATGGCA | 1170 |
| GCAGAAGCAG | GTCAGCTGCA | GTTGAACGTT | 1200 |
| ATGGAGCCGG | TCATTGGCCA | GGCTATGTTC | 1230 |
| GAATCCGTTC | ACATTCTGAC | CAACGCTTGC | 1260 |
| TACAACCTGC | TGGAAAAATG | CATTAACGGC | 1290 |
| ATCACTGCTA | ACAAAGAAGT | GTGCGAAGGT | 1320 |
| TACGTTTACA | ACTCTATCGG | TATCGTTACT | 1350 |

FIG. 2C

```
TACCTGAACC CGTTCATCGG TCACCACAAC      1380

GGTGACATCG TGGGTAAAAT CTGTGCCGAA      1410

ACCGGTAAGA GTGTACGTGA AGTCGTTCTG      1440

GAACGCGGTC TGTTGACTGA AGCGGAACTT      1470

GACGATATTT TCTCCGTACA GAATCTGATG      1500

CACCCGGCTT ACAAAGCAAA ACGCTAAACT      1530

GATGATATCG AACAGTAATC GTACAGGGTA      1560

GTACAAATAA AGAAGGCACG TCAGATGACG      1590

TGCCTTTTTT CTTGTGAGCA GTAACTTAAA      1620

AATAACAACC TAATATCAAC TTGTTAAAAA      1650

ACAAGGAAGG CTAATATGCT AGTTGTAGAA      1680

CTCATCATAG TTTTGCTGGC GATCTTCTTG      1710

GGCGCC                                 1716
```

FIG. 2D

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
       (A) LENGTH:     20 base pairs
       (B) TYPE:       Nucleotide
       (C) STRANDEDNESS: Single
       (D) TOPOLOGY:   Circular (xi) SEQUENCE DESCRIPTION: SEQ ID NO:1:

GGGGATCCTC TAGAGTCGGG                                    20

(2) INFORMATION FOR SEQ ID NO:2:

(i) SEQUENCE CHARACTERISTICS:
       (A) LENGTH:     20 base pairs
       (B) TYPE:       Nucleotide
       (C) STRANDEDNESS: Single
       (D) TOPOLOGY:   Circular (xi) SEQUENCE DESCRIPTION:  SEQ ID NO:2:

GCTCTCAGAG TCTGAACACC                                    20

(2) INFORMATION FOR SEQ ID NO:3:

(i) SEQUENCE CHARACTERISTICS:
       (A) LENGTH:     17 base pairs
       (B) TYPE:       Nucleotide
       (C) STRANDEDNESS: Single
       (D) TOPOLOGY:   Circular (xi) SEQUENCE DESCRIPTION:  SEQ ID NO:3:

CCGGAAGCTT GCATGCC                                            17

(2) INFORMATION FOR SEQ ID NO:4:

(i) SEQUENCE CHARACTERISTICS:
       (A) LENGTH:     18 base pairs
       (B) TYPE:       Nucleotide
       (C) STRANDEDNESS: Single
       (D) TOPOLOGY:   Circular (xi) SEQUENCE DESCRIPTION:  SEQ ID NO:4:

GATGGGTCAG CAGAAAGG                                          18

(2) INFORMATION FOR SEQ ID NO:5:

(i) SEQUENCE CHARACTERISTICS:
       (A) LENGTH:     20 base pairs
       (B) TYPE:       Nucleotide
       (C) STRANDEDNESS: Single
       (D) TOPOLOGY:   Circular (xi) SEQUENCE DESCRIPTION:  SEQ ID NO:5:

TTCATCGGTC ACCAGAACGG                                    20

(2) INFORMATION FOR SEQ ID NO:6:

(i) SEQUENCE CHARACTERISTICS:
       (A) LENGTH:     20 base pairs
       (B) TYPE:       Nucleotide
       (C) STRANDEDNESS: Single
       (D) TOPOLOGY:   Circular (xi) SEQUENCE DESCRIPTION: SEQ ID NO:6:

CAGAATCTGA TGCAGCCGGC                                                   20

(2) INFORMATION FOR SEQ ID NO:7:

(i) SEQUENCE CHARACTERISTICS:
      (A) LENGTH:       22 base pairs
      (B) TYPE:         Nucleotide
      (C) STRANDEDNESS: Single
      (D) TOPOLOGY:     Circular (xi) SEQUENCE DESCRIPTION: SEQ ID NO:7:

CAAAACGCTA AACTGATGAA AG                                                22

(2) INFORMATION FOR SEQ ID NO:8:

(i) SEQUENCE CHARACTERISTICS:
      (A) LENGTH:       477 Amino Acid Residues
      (B) TYPE:         Amino Acid
      (D) TOPOLOGY:     Linear (xi) SEQUENCE DESCRIPTION: SEQ ID NO:8:

```
Ser Asn Asn Ile Arg Ile Glu Glu Asp Leu Leu Gly Thr Arg Glu
1               5                   10                  15

Val Pro Ala Asp Ala Tyr Tyr Gly Val His Thr Leu Arg Ala Ile
                20                  25                  30

Glu Asn Phe Tyr Ile Ser Asn Asn Lys Ile Ser Asp Ile Pro Glu
                35                  40                  45

Phe Val Arg Gly Met Val Met Val Lys Ala Ala Ala Met Ala
                50                  55                  60

Asn Lys Glu Leu Gln Thr Ile Pro Lys Ser Val Ala Asn Ala Ile
                65                  70                  75

Ile Ala Ala Cys Asp Glu Val Leu Asn Asn Gly Lys Cys Met Asp
                80                  85                  90

Gln Phe Pro Val Asp Val Tyr Gln Gly Gly Ala Gly Thr Ser Val
                95                  100                 105

Asn Met Asn Thr Asn Glu Val Leu Ala Asn Ile Gly Leu Glu Leu
                110                 115                 120

Met Gly His Gln Lys Gly Glu Tyr Gln Tyr Leu Asn Pro Asn Asp
                125                 130                 135

His Val Asn Lys Cys Gln Ser Thr Asn Asp Ala Tyr Pro Thr Gly
                140                 145                 150

Phe Arg Ile Ala Val Tyr Ser Ser Leu Ile Lys Leu Val Asp Ala
                155                 160                 165

Ile Asn Gln Leu Arg Glu Gly Phe Glu Arg Lys Ala Val Glu Phe
                170                 175                 180

Gln Asp Ile Leu Lys Met Gly Arg Thr Gln Leu Gln Asp Ala Val
                185                 190                 195

Pro Met Thr Leu Gly Gln Glu Phe Arg Ala Phe Ser Ile Leu Leu
                200                 205                 210

Lys Glu Glu Val Lys Asn Ile Gln Arg Thr Ala Glu Leu Leu Leu
                215                 220                 225

Glu Val Asn Leu Gly Ala Thr Ala Ile Gly Thr Gly Leu Asn Thr
                230                 235                 240

Pro Lys Glu Tyr Ser Pro Leu Ala Val Lys Lys Leu Ala Glu Val
                245                 250                 255

Thr Gly Phe Pro Cys Val Pro Ala Glu Asp Leu Ile Glu Ala Thr
```

-continued

```
                    260                 265                 270
Ser Asp Cys Gly Ala Tyr Val Met Val His Gly Ala Leu Lys Arg
                275                 280                 285
Leu Ala Val Lys Met Ser Lys Ile Cys Asn Asp Leu Arg Leu Leu
                290                 295                 300
Ser Ser Gly Pro Arg Ala Gly Leu Asn Glu Ile Asn Leu Pro Glu
                305                 310                 315
Leu Gln Ala Gly Ser Ser Ile Met Pro Ala Lys Val Asn Pro Val
                320                 325                 330
Val Pro Glu Val Val Asn Gln Val Cys Phe Lys Val Ile Gly Asn
                335                 340                 345
Asp Thr Thr Val Thr Met Ala Ala Glu Ala Gly Gln Leu Gln Leu
                350                 355                 360
Asn Val Met Glu Pro Val Ile Gly Gln Ala Met Phe Glu Ser Val
                365                 370                 375
His Ile Leu Thr Asn Ala Cys Tyr Asn Leu Leu Glu Lys Cys Ile
                380                 385                 390
Asn Gly Ile Thr Ala Asn Lys Glu Val Cys Glu Gly Tyr Val Tyr
                395                 400                 405
Asn Ser Ile Gly Ile Val Thr Tyr Leu Asn Pro Phe Ile Gly His
                410                 415                 420
His Asn Gly Asp Ile Val Gly Lys Ile Cys Ala Glu Thr Gly Lys
                425                 430                 435
Ser Val Arg Glu Val Val Leu Glu Arg Gly Leu Leu Thr Glu Ala
                440                 445                 450
Glu Leu Asp Asp Ile Phe Ser Val Gln Asn Leu Met His Pro Ala
                455                 460                 465
Tyr Lys Ala Lys Arg Tyr Thr Asp Glu Ser Glu Gln
                470                 475
```

MUTANT ASPARTASE AND THE PREPARATION THEREOF

FIELD OF THE INVENTION

The subject invention relates to mutant aspartases, and the preparation process thereof.

BACKGROUND OF THE INVENTION

A dipeptyl sweetener, L-aspartyl-L-phenylalanine methyl ester, also known as aspartame, has been developed and commercialized. The demand of L-aspartic acid for use in the production of the sweetener has been increasing dramatically all over the world in recent years.

Aspartase (L-aspartate ammonia-lyase, EC 4.3.1.1) is an enzyme which catalyzes the reversible conversion of fumaric acid and ammonia to L-aspartic acid, as well as the reverse reaction of deamination of L-aspartic acid:

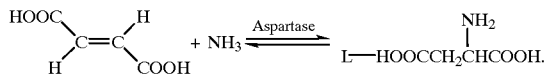

Yumoto et al., *Physiol. Chem. Phys.* 14:391–397 (1982) reported that the activity of aspartase from *E. coli* was enhanced 1.4–3.8 fold by limited proteolysis. The enhancement of activity was resulted from the cleavage of a peptide bond at certain region centered at arginine from the carboxy-terminal.

Murase et al., *Biochem. Biophys. Res. Commun.* 177:414–419 (1991) disclosed a mutant aspartase wherein the cysteine residue at position 430 in the amino acid sequence of the wild-type enzyme was substituted with tryptophan by site-directed mutagenesis. The catalytic activity of the mutant was 134% of that of the wild-type enzyme tinder standard assay conditions.

Zhang et al., *Biochem. Biophys. Res. Commun.* 192:15–21 (1993) described a mutant aspartase with 3.7-fold increase in catalytic activity than that of the wild-type enzyme. The mutant was prepared by site-directed mutagenesis to have an arginine residue at 126 position instead of lysine occurring, in the wild-type enzyme.

All these references are hereby incorporated by reference in their entirety and specific pertinent parts.

Despite of the above, there is a continuing need for new mutant aspartases with enhanced catalytic activity useful for efficiently producing L-aspartic acid.

SUMMARY OF THE INVENTION

The object of the invention is to provide mutant aspartases which have a higher catalytic activity.

Accordingly, the invention relates to mutant aspartases comprising the amino acid sequence of a wild-type aspartase wherein the amino acid residue at one of positions 25, 123, 421 and 463 is substituted.

In another aspect, the invention relates to a method for preparing the mutant aspartases of the invention.

BRIEF DESCRIPTION OF THE DRAWINGS

FIGS. 1A–1B The amino acid sequence (SEQ ID NO: 8) of wild-type aspartase of *E. coli* B.

FIG. 2 The DNA sequence (SEQ ID NO: 9) coding for wild-type aspartase of *E. coli* B.

FIGS. 3A–3B the nucleotide sequence of the untranscribed in aspA of *E. coli* B (SEQ ID NO: 9) as taught in the Republic of China patent publication No: 153674 and the corresponding amino acid sequence of SEQ ID NO: 8.

DETAILED DESCRIPTION OF THE INVENTION

The invention in the first aspect provides mutant aspartases comprising the amino acid sequence of a wild-type aspartase wherein the amino acid residue at one of positions 25, 123, 421 and 463 is substituted.

As used herein, the term "mutant aspartase" refers to an enzyme exhibiting the activity of aspartase and having one or more amino acid residues in the sequence which are different from that occurring in the wild-type sequence.

As used herein, the term "wild-type aspartase" or "wild-type enzyme" refers to a full length aspartase isolated from naturally-occurring *E. coli*, e.g. *E. coli* K-12, *E. coli* W and *E. coli* B as described in Guest et al., *J. Gen. Microbiol.* 130: 1271–1278 (1981), Takagi et al., *Nucl. Acids Res.* 13: 2063–2074 (1985), Liu et al., *Proceedings of the 7th Federation of Asian and Oceanian Biochemists Symposium*, Nov. 28–30, 1988 and ROC Patent Publication No. 153674, or its fragment wherein certain amino acid residues at the carboxy-terminal have been deleted, e.g. those described in Yumoto et al., (1982), supra. ROC Patent Publication No. 153674 depicts the nucleotide sequence (SEQ ID NO: 9) of the untranscribed strand in asp A of *E. coli* (FIG. 3). All these references are hereby incorporated by reference in their entirety and specific pertinent parts. Substitutions of residues within an amino acid sequence with functionally and/or structurally equivalent amino acids may result in silent changes. The invention also encompasses such silent mutations.

In one embodiment of the invention, the wild-type aspartase has the amino acid sequence as shown in FIG. 1 (SEQ ID NO: 8).

In another embodiment of the invention, the wild-type aspartase has an sequence as shown in FIG. 1 (SEQ ID NO: 8) with one to seventeen amino acid residues at positions 461 to 477 being optionally deleted. Preferably, the amino acid residues at positions 471 to 477 are deleted.

There are totally twenty L-α-amino acids which structurally constitute proteins, viz. glycine (Gly), alanine (Ala), valine (Val), leucine (Leu), isoleucine (Ile), serine (Ser), threonine (Thr), cysteine (Cys), methionine (Met), aspartic acid (Asp), glutamic acid (Glu), asparagine (Asn), glutamine (Gln), arginine (Arg), lysine (Lys), histidine (His), phenylalanine (Phe), tyrosine (Tyr), tryptophan (Trp), and proline (Pro). In accordance with the invention, the amino acid substituting for the residue occurring in wild-type aspartases or their variants at positions 25, 123, 421 and 463 can be any of the other nineteen protein-constituting amino acids.

For instance, in the embodiment of the invention wherein the wild-type aspartase has the sequence as shown in FIG. 1 (SEQ ID NO: 8), the amino acid residues at positions 25, 123, 421 and 463 are all His. The amino acid substituting for the His residue may therefore be selected from Gly, Ala, Val, Leu, Ile, Ser, Thr, Cys, Met, Asp, Glu, Asn, Gln, Arg, Lys, Phe, Tyr, Trp, and Pro.

In a preferred embodiment of the invention, the mutant aspartases comprise a Gln residue at one of positions 25, 123, 421 and 463 in the amino acid sequence. In the most preferred embodiment of the invention, the mutant aspartase comprises the amino acid sequence of a wild-type aspartase wherein the amino acid residue at position 25 is Gln.

In the following text of the specification, the mutation in the mutant aspartases of the invention will be designated in conformity with the mutation position (site) and the substituting amino acid for His residue as "substituting amino acid$^{position}$" or "His$^{position}$-to-substituting amino acid" mutants. Accordingly, the mutant aspartases comprising a Gln at position 25, 123, 421 or 463 will be abbreviated as Gln$^{25}$, Gln$^{123}$, Gln$^{421}$ or Gln$^{463}$ mutant, or His$^{25}$-to-Gln, His$^{123}$-to-Gln, His$^{421}$-to-Gln or His$^{463}$-to-Gln mutant, respectively.

The invention also provides a method for producing the mutant aspartases of the invention, said method comprising the step of culturing a suitable host cell transformed with the DNA sequence coding for the mutant aspartases of the invention.

The DNA sequence coding for the mutant aspartases of the invention can be readily determined by persons skilled in the art based on the sequence encoding the target wild-type enzyme and the knowledge of genetic code. For instance, the codon CAC or CAT encoding a His residue at the site of interest in the DNA sequence of the wild-type enzyme can be substituted with CAA or CAG if a His-to-Gln mutation is desired. The desirable full length sequence encoding the mutant aspartases of the invention may then be prepared by conventional methods and used to transform a suitable host cell for expressing the desired mutants.

The methods for synthesizing DNAs of specified sequence are well-known by persons skilled in the art. For instance, Hunkapiller et al., *Nature*, 310:105–111 (1984), Itakura et al., *Ann. Rev. Biochem.*, 53:323–356 (1984) and Caruthers, *Science*, 230:281–285 have described methods for automated synthesis of DNA. The DNA sequence coding for the mutant aspartases of the invention may therefore be conveniently synthesized by automatic solid-phase synthesis.

Alternatively, the DNA sequence coding for the mutant aspartases of the invention may be generated from the sequence coding for wild-type aspartases by mutation.

Site-directed mutagenesis is a technique that alters the amino acid sequence at a specific position within a protein by changing the genetic material coding for the protein. It is particularly suitable for producing the DNA sequences encoding mutant proteins with single amino acid substitutions. Accordingly, the DNA sequence coding for the mutant aspartases of the invention can be conveniently, and most preferably, generated from the sequence of the wild-type aspartase by site-directed mutagenesis. In the embodiments of the invention, the DNA sequence of interest is generated as described in Kunkel, *Proc. Natl. Acad. Sci. U.S.A.* 82: 488–492 (1985) and Picard et al., *Nucleic Acids Research*, 22: 2587–2591 (1994). (Both references are hereby incorporated by reference in their entirety and specific pertinent parts.)

Typically, a mutagenic oligonucleotide printer containing a mismatched nucleotide is used to result in the desired mutation. Similar to the determination of the full length DNA sequence encoding the mutant aspartases of the invention as described above, the mutagenic oligomers can also be readily designed in accordance with the base sequence of the target wild-type enzyme and the knowledge of genetic code. For instance, if a His-to-Gln mutation is desired, an oligomer composed of the base sequence in the vicinity of the site to be altered in the wild-type target wherein the codon CA<u>C</u> or CA<u>T</u> is changed to CA<u>G</u> or CA<u>A</u> can be properly used.

In the following text of the specification, the gene coding for aspartases will be referred to as "aspA." That coding for mutant aspartases of the invention will be referred to as "mutant aspA" or designated in conformity with the mutation position (site) and the substituting amino acid as "aspamino acid$^{position}$." Accordingly, the gene encoding the Gln$^{25}$, Gln$^{123}$, Gln$^{421}$ and Gln$^{463}$ mutants will be designated as aspGln$^{25}$, aspGln$^{123}$, aspGln$^{421}$ and aspGln$^{463}$, respectively.

The DNA sequence of aspA for generating that encoding a mutant aspA by site-directed mutagenesis can be prepared as described in Guest et al., (1981), Takagi et al., (1985), Liu et al., (1988) and ROC Patent Publication No. 153674, Supra. In one embodiment of the invention, the plasmid pAC2 prepared in accordance with ROC Patent Publication No. 153674 was used as the target for mutagenesis. In another embodiment of the invention, the plasmid pGB5 described in Liu et al., (1988) was used as the target for mutagenesis. Both plasmids carry the 1.7 kb aspA of *E. coli* B. The relevant nucleotide sequence is as depicted in FIG. 2 (SEQ ID NO: 9).

When a mutation in the fragment of a wild-type aspartase wherein certain amino acid residues at the carboxy-terminal are deleted, e.g. those described in Yumoto et al., (1982), Supra is desired, the deletion of the amino acid residues at carboxy-terminal can be appropriately fulfilled by introducing a stop-codon at a desired position. In accordance with the invention, the DNA sequence coding for the mutant can be constructed either by first introducing into a full length aspA a stop-codon, e.g. an ochre-mutation, at the desired position near the carboxy-terminal and then making a mutation at position 25, 123, 421 or 463, or by introducing the stop-codon into aspGln$^{25}$, aspGln$^{123}$, aspGln$^{421}$ and aspGln$^{463}$. In the following text of the specification, the mutants encoded by DNA sequences comprising the above double-point mutations will be designated as e.g. Gln$^{25}$&Ochre$^{471}$ mutant. The Ochre$^{471}$ mutant has 471 amino acid residues as a result of an ochre mutation.

Once the DNA sequences coding for the mutants of the invention are prepared, it can be directly used to transform a suitable host cell or by the aid of a suitable vector. The term "suitable vector" used herein refers to those conventionally used in genetic engineering techniques. Vectors suitable for use with an *E. coli* expression system include, but not limited to, those to having a promoter such as PL, T5, T7, SP6, Ptac, lac and trp, etc.

The term "suitable host cell" used herein refers to the cell conventionally used in genetic engineering techniques for recombinantly producing proteins. They include, but not limited to, bacteria, such as Bacillus and Escherichia. Preferably, the host cell is *E. coli*.

The mutant aspartases of the invention exhibit an enhanced catalytic activity and thus can be used for efficiently producing, L-aspartic acid. For this purpose, the mutant aspartases expressed by the host cells can be purified to high purity by conventional methods, e.g. chromatography.

Alternatively, the culture broth of the host cells, the host cells collected from the culture, or the processed material of the host cells can be directly used for the production of L-aspartic acid.

The following examples will illustrate the subject invention more detailedly. These examples, however, are not to be construed as a limitation of the invention.

EXAMPLE 1

Preparation of Gln$^{25}$ Mutant

The pAC2 plasmid was prepared in accordance with ROC Patent Publication No. 153674 and used as the target for site-directed mutagenesis.

One-tube PCR:
Stage 1:
A 100 µl mixture containing the following was used to proceed reaction at 94° C. for 1 minute, 50° C. for 1 minute, and 72° C. for 2 minutes: 10 ng DNA from plasmid pAC2, 10 pmole N-terminal primer of the sequence: 5' GGGGATC-CTCTAGAGTCGGG 3' (SEQ ID NO: 1), 10 pmole mutagenic primer of the sequence as shown in Table 1, 0.2 mM dNTP, 10 µl 10× X PFU buffer (Stratagene, USA) and 2.5 U cloned PFU DNA polymerase (Stratagene, USA). The reaction cycle was repeated 10 times, followed by a reaction at 72° C. for 5 minutes.

TABLE 1

Mutagenic Primer for Gln$^{25}$ Mutant

| Mutant | Sequence (5' 3')[a] |
|---|---|
| Gln$^{25}$ | GCTCTCAGAGTCTGAACACC[b] (SEQ ID NO:2) | a. The asterisk marks the mismatched base.
b. The sequence is in the reverse direction.

Stage 2:
To the above reaction mixture was added 50 pmole of C-terminal primer of the sequence: 5' CCGGAAGCTTG-CATGCC 3' (SEQ ID NO: 3). PCR was proceeded under the same conditions as Stage 1.

Stage 3:
To the reaction mixture of Stage 2 was added 50 pmole N-terminal primer. PCR was proceeded under the same conditions as Stage 1.

Recovery of PCR Product
PCR products were separated by 0.8% agarose gel electrophoresis. A 1.7 kb DNA fragment was cut from the gel. The DNA was recovered with GeneClean II kit (Bio 101).

Subcloning in $E.$ $coli$ N4830
The recovered PCR product, a 1.7 kb DNA fragment, was subcloned under the control of $P_L$ promoter in vector pLB prepared as described in ROC Publication No. 153674. The cloning site was XbaI. The subcloning procedures are as follows:

First, 2 µg of the PCR product was added to a 50 µl reaction solution (containing 50 mM Tris-HCl, 10 mM MgCl$_2$, 100 mM NaCl, 1 mM dithiothreitol, pH 7.5). The mixture was added with 10 U XbaI restriction enzyme and incubated at 37° C. for 2 hours. The DNA was isolated from the mixture with GeneClean II Kit.

To 40 µl of the above reaction mixture was added 5 µg pLB. The plasmid was linearized with 20 U XbaI restriction enzyme by incubating at 37° C. for 2 hours. The reaction mixture was added with 6 µl of 10× dephosphorylation buffer (Boehringer Manneheim GmbH) and the volume was adjusted to 60 µl with distilled water. The dephosphorylation reaction was proceeded with 1 U alkaline phosphatase at 37° C. for 30 minutes. The linearized pLB vector was recovered from the mixture with GeneClean II Kit.

Thereafter, 300 ng of the XbaI digested PCR product was ligated with 500 ng of the XbaI linearized and dephosphorylated pLB vector in 20 µl reaction (50 mM Tris-HCl, 10 mM MgCl$_2$, 10 mM dithiothreitol, and 0.3 mM ATP, pH 7.5). The mixture was incubated with 1 U T4 DNA ligase at 12° C. overnight.

Frozen competent cells were prepared following the protocol described in Simanis et al., $DNA$ $Cloning$ $II:$ 121–125 (1985). Aliquots of 0.2 ml of $E.$ $coli$ N4830 (Pharmacia Biotech) competent cells were put in Eppendorf tubes and frozen at −70° C. Transformation was proceeded by adding 10 µl ligation mixture to pre-thawed competent cells. The mixture was incubated on ice for 30 minutes, heat-shocked at 42° C. for 2 minutes, and returned to ice. LB broth (0.8 ml, containing 10 mg tryptone, 5 mg yeast extract and 10 mg NaCl per ml) was added to the cold mixture. The mixture was incubated with shaking at 37° C. for 1 hour. The cell culture (50 or 100 µl was spread onto LB plate (containing 100 µg ampicillin/ml). The plate was inverted and incubated at 37° C. overnight.

Finally, the desired recombinant clone was screened by identifying the restriction map of the clones and confirmed by DNA sequencing according to Sanger's method ($Proc.$ $Natl.$ $Acad.$ $Sci.$ $USA,$ 74: 5463–5467 (1977)).

The resultant pAH25Q (in $E.$ $coli$ N4830) was deposited in the Food and Industry Research Development Institute (FIRDI, Shinshu, Taiwan, ROC) on Jan. 27, 1997, with the accession No. 940142.

EXAMPLE 2

Preparation of Gln$^{123}$, Gln$^{421}$ and Gln$^{463}$ Mutants

The preparation of the three single-point mutants, Gln$^{123}$, Gln$^{421}$ and Gln$^{463}$, was proceeded by site-directed mutagenesis as described by Kunkel (1985), Supra, using M13 (mp19-aspA) recombinant phage as the target. The M13 (mp19-aspA) recombinant phage was constructed by cloning the wild-type aspA gene from plasmid pGB5 in $E.$ $coli$ HB 101 (Liu et al., (1988), supra to the M13 mp19 RF DNA (Boehringer Mannheim GmbH) using AvaI and HindIII as cloning sites.

The detailed procedures for constructing the M13 recombinant phages are described in steps (a) to (f) as follows:
(a) Isolation of aspA Gene Fragment
The plasmid pGB5 was treated according to the method of CsCl/EtBr density gradient centrifugation described in Ausubel et al., $Current$ $Protocols$ $in$ $Molecular$ $Biology$ 1.7.1–1.7.4 (1987).

The plasmid pGB5 (30 µg) was digested by AvaI and HindIII (each 30 U) in a 50 µl reaction mixture containing 10 mM Tris-HCl, 5 mM MgCl$_2$, 100 mM NaCl and 1 mM 2-mercaptoethanol (pH 8.0). The reaction mixture was incubated at 37° C. for 2 hours. Two fragments were obtained, which were separated by 0.8% agarose gel electrophoresis. The 1.7 kb fragment containing aspA gene was eluted from the gel by GeneClean II Kit (Bio 101).

(b) Linearization of M13 mp19 RF DATA
M13 mp 19 RF DNA (200 ng) was added to a 10 µl reaction mixture containing similar components as described in (a). The mixture was then mixed with 10 U of both AvaI and HindIII restriction enzymes and incubated at 37° C. for 10 minutes.

(c) Ligation
The AvaI and HindIII linearized M13 mp19 RF DNA obtained in step (b) (100 µl) and the 1.7 kb aspA gene fragment obtained in step (a) (300 ng) was added to a 20 µl reaction mixture containing 50 mM Tris-HCl, 10 mM MgCl$_2$, 10 mM dithiothreitol, and 0.5 mM ATP (pH 7.5). The mixture was incubated with 1 U of T4 DNA ligase at 12° C. overnight.

(d) Transformation
Frozen competent cells of $E.$ $coli$ MV1190 (BioRad) were prepared following the protocol described in Simanis et al., $DNA$ $Cloning$ $II:$ 121–125 (1985). Aliquots of 0.2 ml mixture were added to Eppendorf tubes and frozen to −70° C. for later use.

Before transformation, one tube of the frozen competent cells was thawed at room temperature, and added with 10 µl of the ligation mixture obtained in step (c). The mixture was incubated on ice for 30 minutes, heat-shocked at 42° C. for 2 minutes, and then returned to ice. LB broth (0.8 ml) was added to the cold mixture. The mixture was incubated with shaking at 37° C. for 1 hour.

(e) Plating and Screening Recombinant Phage on X-gal Plate

The cell mixture obtained in step (d) (50 μl), overnight culture of *E. Coli* MV1190 (0.3 ml), 100 mM IPTG (40 μl), 2% X-gal (40 μl) and melt and warmed top agar (5 ml) were added to an autoclaved glass tube. The mixture was poured immediately on a pre-warmed H plate (containing 10 mg tryptone, 8 mg NaCl and 15 mg agar per ml) and allowed to stand at room temperature to let the top agar hardened. The plate was then inverted and incubated at 37° C. overnight.

On the following day, there were two kinds of plaques on the X-gal plate. Yellow tip was used to withdraw white plaques from the plate. Each agar cylinder was resuspended in 1 ml TE buffer (containing 10 mM Tris-HCl and 0.1 mM EDTA, pH 7.0) in Eppendorf tube. The phage/TE solution was stored at 4° C. before use.

(f) Restriction Map Analysis

The *E. coli* MV1190 cells were infected with the phages obtained in step (c). The double-stranded DNA from *E. coli* cells was harvested for restriction map checking.

The phage/TE solution obtained in step (e) (30 μl) was added to 3 ml LB broth containing 30 μl of *E. coli* MV 1190 overnight culture. The cell culture was incubated with shaking at 37° C. overnight, followed by centrifugation. The pellet of bacteria was recovered and used to make double-stranded DNA by minilysis method for making plasmid DNA given in Maniatis et al., *Molecular Cloning* (1982). The double-stranded DNA from bacteria was digested with AvaI and HindIII restriction enzymes, and separated by 0.8% agarose gel electrophoresis. The desired clone showed a 1.7 kb DNA band on the gel.

By proceeding from steps (a) to (f), the recombinant M13 (mp19-aspA) was constructed and ready for further working on site-directed mutagenesis in aspA by Kunkel's method. The procedures of the Kunkel's site-directed mutagenesis were described below.

(g) Growing of U-Containing Phage

To 10 ml LB broth was added 30 μl/ml chloramphenicol, 0.25 μg/ml uridine, 100 μl overnight culture of *E. coli* CJ236 (Biorad), and a proper titer of M13 (mp19-aspA) recombinant phage obtained in step (f) to make the multiplicity of infection below 0.1. The culture was incubated at 37° C. with shaking for 6–8 hours and then spun at 1.3 krpm for 10 minutes. The supernatant was transferred to a fresh tube and centrifuged again.

The titer on the *E. coli* CJ236 over that on the *E. coli* MV1190 was higher than $10^5$.

(h) Isolation of U-Containing Single-Stranded DNA

To an Eppendorf tube containing 1.3 ml supernatant obtained in step (g), there was added 330 μl of 2% $PEG_{6000}$/2.5 M NaCl to precipitate the phage. The mixture was incubated on ice for 15 minutes, and spun at 1.3 krpm for 15 minutes. All traces of supernatant were removed. The phage pellet was resuspended in 300 μl TE buffer (pH 7.0).

The phage/TE solution was extracted once with phenol, once with phenol:chloroform:isoamyl alcohol (25:24:1), and once with chloroform:isoamyl alcohol (24:1). To the mixture was added 0.1 volume of 3 M sodium acetate (pH 5.2) and 2.5 volume of ethanol to precipitate DNA. The mixture was frozen to −20° C. overnight, and spun. The pellet was washed with 90% ethanol, and resuspend in TE buffer (pH 7.0).

(i) Phosphorylation of Mutagenic Oligonucleotide

A 30 μl reaction mixture containing 3 μl 10× PNK buffer, 30 mM ATP, 1 U T4 DNA polynucleotide kinase (all purchased from Boehringer Mannheim GmbH), and 150 pmole of proper mutagenic oligonucleotide as shown in Table 2 below was incubated at 37° C. for 1 hour, heated to 65° C. for 10 minutes, and then frozen to −20° C. before use.

TABLE 2

Mutagenic Oligonucleotides for $Gln^{123}$, $Gln^{421}$ and $Gln^{463}$

| Mutants | Sequence (5'~3')[a] |
|---|---|
| $Gln^{123}$ | GATGGGTCAGCAGAAAGG[b]   (SEQ ID NO:4)   (mismatch marked *) |
| $Gln^{421}$ | TTCATCGGTCACCAGAACGG[b]   (SEQ ID NO:5) |
| $Gln^{463}$ | CAGAATCTGATGCAGCCGGC[b]   (SEQ ID NO:6) | a. The asterisks mark the mismatched bases.
b. The sequences are in the forward direction.

(j) In Vitro Synthesis of Mutagenic Strand DNA

The 5'-phosphorylated oligonucleotides obtained in step (i) were annealed to the M13 (mp19-aspA) U-containing single-stranded DNA obtained in step (h).

A 10 μl annealing mixture of 3 pmole of the 5'-phosphorylated oligonucleotide, 500 ng of M13 U-containing single-stranded DNA, and 1 μl 10× annealing buffer (containing 200 mM Tris-HCl, 100 mM $MgCl_2$, 500 mM NaCl and 10 mM DTT, pH 7.5) was incubated at 70° C. for 10 minutes, and slowly cooled down below 30° C.

To the 10 μl of the annealing mixture was added 2 μl 10× synthesis salt solution (containing 100 mM Tris-HCl, 50 mM $MgCl_2$ and 20 mM DTT), 0.5 mM each dNTP, 1 mM ATP, 1 U T4 DNA ligase, 1 U T4 DNA polymerase (all purchased from Boehringer Mannheim GmbH), and distilled water to a final 20 μl of reaction volume. The reaction was incubated at 37° C. for 90 minutes. Another 1 U T4 DNA ligase was added. The mixture was incubated at 12° C. overnight.

(k) Transformation and Plating

One tube of *E. coli* MV1190 competent cells frozen at −70° C. was allowed to thaw at room temperature, and then added with 10 μl of the synthesis mixture obtained in step (j). The mixture was incubated on ice for 30 minutes, heat-shocked at 40° C. and returned to ice, followed by adding with 0.8 ml LB broth. The culture was incubated at 37° C. for 1 hour.

To an autoclaved glass tube, was added 50 μl of the transformants, 0.3 ml overnight culture of *E. coli* MV1190 and 5 ml melt and warmed top agar. The mixture was immediately poured onto an H plate, and allowed to stand at room temperature to let the top agar harden. The plate was then inverted and incubated at 37° C. overnight. Yellow tip was used to collect each plaque from the plate. Each agar cylinder was suspended in 1 ml TE buffer (pH 7.0) in Eppendorf tube. The phage/TE solution was stored at 4° C. for further screening the mutant.

(l) Mutant Screening by DNA Sequence Analysis

The single-stranded DNA from M13 phages collected in step (k) was isolated and the DNA sequences thereof were analyzed.

To each 1.5 ml LB broth, there was added 150 μl overnight culture of *E. coli* MV1190 and 200 μl of the phage/TE solution obtained in step (k). The culture was incubated with shaking at 37° C. for 6–8 hours.

The single-stranded DNA was prepared with a similar procedure as that described in step (h) for preparing the U-containing single-stranded DNA.

The sequence of the single-stranded DNA was analyzed by Sanger's dideoxy-chain termination method using ABI PRISM Dye Terminator Cycle Sequencing Ready Reaction Kit (PERKIN ELMER). The PCR Cycle sequencing program and the PCR product treatment for sequence analysis all followed the procedures described in the User's manual.

Following the procedures of steps (g) to (l), the three single-point mutants, M13 (containing mp19-aspGln$^{123}$), M13 (containing mp19-aspGln$^{421}$) and M13 (containing mp19-aspGln$^{463}$) were constructed.

(m) Subcloning of the Mutant aspA Genes into pLB Vector

The mutant aspA genes (aspGln$^{123}$, aspGln$^{421}$ and aspGln$^{463}$) were subcloned to pLB vector to highly express mutant aspartases in *E. coli* N4830 (Pharmacia). The pLB vector was prepared by inserting the EcoRI-HaeIII fragment of λP$_L$ GenBlock (Pharmacia) into the restriction sites EcoI and SmaI of plasmid pGem4 (Promega Biotec), digesting the resultant plasmid with BamHI, and ligating the blunt ends with T4 DNA ligase.

The cloning sites used to subclone aspGln$^{123}$, aspGln$^{421}$ and aspGln$^{463}$ into pLB vector were AvaI and HindIII. The subcloning strategy was as follows:

To isolate the 1.7 kb fragment containing mutant aspGln$^{123}$, aspGln$^{421}$, aspGln$^{463}$, the double-stranded DNA of the mutant M13 phage shown in step (l) was cut with AvaI and HindIII, the mixture was applied onto 0.8% agarose gel for electrophoresis, and the 1.7 kb DNA fragments were finally eluted from the gel by GeneClean II Kit (Bio 101). The pLB vector was linearized with AvaI and HindIII restriction enzymes and dephosphorylated by alkaline phosphatase. The linear pLB vector was ligated with 1.7 kb DNA fragment using T4 DNA ligase. The ligation mixture was used to transform the frozen competent cells of *E. Coli* N4830. The recombinants were screened by checking the size and the restriction map of the clones.

By the strategy described above, three recombinant clones, pAH123Q, pAH421Q and pAH463Q, were constructed and ready for producing mutant aspartases in *E. coli* N4830 for the further study of the catalytic activity of the mutant aspartases.

EXAMPLE 3

Preparation of Ochre$^{471}$ and Gln$^{25}$ & Ochre$^{471}$ Mutants

Following a similar procedure as described in EXAMPLE 2, the single-point mutant Ochre$^{471}$ and the double-point mutant Gln$^{25}$ & Ochre$^{471}$ were constructed using the mutagenic nucleotide shown in Table 3 below. The M13 (mp19-aspA) recombinant phages prepared as described in EXAMPLE 2 was used as the target for the single mutant. The mutant aspGln$^{25}$ gene from pAH25Q (in *E. coli* N4830) obtained in EXAMPLE 1 was cloned to the M13 mp19 RF DNA using BamHI as the cloning site, and the resultant M13 (mp19-aspGln$^{25}$) recombinant phage used as target for the double-point mutant.

TABLE 3

Mutagenic Oligonucleotide for Ochre$^{471}$

| Mutant | Sequence (5'~3')[a] |
|---|---|
| | * |
| Ochre$^{471}$ | CAAAACGCTAAACTGATGGAAAG[b] (SEQ ID NO:7) | a. The asterisks mark the mismatched bases.
b. The sequence is in the forward direction.

Recombinant clones Y4710 and pAH25Q&Y4710 were obtained. The later was deposited in the FIRDI on Jan. 27, 1997, with the accession No. 940143.

EXAMPLE 4

Specific Activity Test

The enhanced activity of the mutant aspartases of the invention over that of the wild-type enzyme was confirmed by the following test:

To an 1 ml substrate containing 0.1 M L-aspartate, 0.1 M Tris-HCl (pH 7.4), and 2 mM MgCl2 was added an appropriate amount of enzyme. The production rate of fumarate was tested at 30° C. The mole number of fumarate generated was calculated by absorbance at 240 nm, using $\epsilon_m$=2.53 M$^{-1}$cm$^{-1}$. The amount of enzyme needed under these assay conditions to generate 1 μmole of fumarate per minute was defined as the activity unit (U). The specific activity (U/mg) of the enzyme was calculated as the units per 1 mg of protein tested under the standard assay conditions at 30° C. The results are shown in Table 4.

TABLE 4

The Specific Activity of Wild-type and Mutant Aspartases

| Aspartases | Specific activity (U/mg)[a] | Relative activity (%) |
|---|---|---|
| Wild-type | 6.1 | 100 |
| Gln$^{25}$ | 25.2 | 413 |
| Gln$^{123}$ | 6.5 | 107 |
| Gln$^{421}$ | 9.7 | 159 |
| Gln$^{463}$ | 6.9 | 131 |

[a]The activity of aspartase was assayed in the deamination direction. The reaction mixture contained 100 mM Na-L-aspartate, 2 mM MgCl$_2$ and 100 mM Tris-HCl buffer (pH 7.4).

EXAMPLE 5

In a test similar to EXAMPLE 4, the enhanced activity of the mutant aspartase of the invention over that of wild-type enzyme is further confirmed.

TABLE 5

A Comparison of the Specific Activity of Wild-type and Mutant Aspartases

| Aspartases | Specific activity (U/mg)[a] | Relative activity (%) |
|---|---|---|
| Wild-type | 28.1 | 100 |
| Gln$^{25}$ & Ochre$^{471}$ | 90.77 | 323 |
| Ochre$^{471}$ | 75.8 | 270 |

[a]The activity of aspartase was assayed in the deamination direction. The reaction mixture contained 100 mM Na-L-aspartate, 2 mM MgCl$_2$ and 100 mM Tris-HCl buffer (pH 9.0).

What is claimed is:

1. A mutant aspartase comprising the amino acid sequence of wild-type *Escherichia coli* aspartase wherein the amino acid residue at one of positions 25, 123, 421 and 463 of SEQ ID NO: 8 is substituted.

2. The mutant aspartase according to claim 1, wherein one to seventeen amino acid residues at positions 461 to 477 are deleted.

3. The mutant aspartase according to claim 2, wherein amino acid residues at positions 471 to 477 are deleted.

4. The mutant aspartase according to claim 1, 2 or 3, wherein the amino acid residue at position 25 is Gln.

5. The mutant aspartase according to claim 1, 2, or 3 wherein the amino acid residue at position 123 is Gln.

6. The mutant aspartase according to claim 1, 2, or 3 wherein the amino acid residue at position 421 is Gln.

7. The mutant aspartase according to claim 1, 2, or 3 wherein the amino acid residue at position 463 is Gln.

* * * * *